United States Patent
Van der Watt et al.

(10) Patent No.: US 9,737,420 B2
(45) Date of Patent: Aug. 22, 2017

(54) ALIGNMENT ADAPTER FOR PROSTHETIC SPORT FEET

(71) Applicant: Ossur hf, Reykjavik (IS)

(72) Inventors: Francois Van der Watt, Winnie, TX (US); Christophe Lecomte, Reykjavik (IS)

(73) Assignee: Ossur hf, Reykjavik (IS)

( * ) Notice: Subject to any disclaimer, the term of this patent is extended or adjusted under 35 U.S.C. 154(b) by 0 days.

(21) Appl. No.: 14/978,282

(22) Filed: Dec. 22, 2015

(65) Prior Publication Data

US 2016/0106556 A1 Apr. 21, 2016

Related U.S. Application Data

(62) Division of application No. 13/928,210, filed on Jun. 26, 2013, now abandoned.

(60) Provisional application No. 61/665,162, filed on Jun. 27, 2012.

(51) Int. Cl.
*A61F 2/78* (2006.01)
*A61F 2/76* (2006.01)
*A61F 2/50* (2006.01)

(52) U.S. Cl.
CPC .............. *A61F 2/76* (2013.01); *A61F 2/78* (2013.01); *A61F 2002/5016* (2013.01); *A61F 2002/7868* (2013.01)

(58) Field of Classification Search
CPC ....................................................... A61F 2/76
See application file for complete search history.

(56) References Cited

U.S. PATENT DOCUMENTS

| | | | |
|---|---|---|---|
| 4,007,496 A | * | 2/1977 | Glabiszewski ........... A61F 2/66 623/27 |
| 4,149,280 A | | 4/1979 | Wilson |
| 4,923,476 A | | 5/1990 | Cooper et al. |
| 4,994,086 A | | 2/1991 | Edwards |

(Continued)

FOREIGN PATENT DOCUMENTS

WO     WO 95/25488 A1     9/1995

OTHER PUBLICATIONS

International Search Report and Written Opinion for PCT Application No. PCT/US2013/047961 filed on Jun. 26, 2013, dated Oct. 23, 2013.

(Continued)

*Primary Examiner* — Jacqueline Woznicki
(74) *Attorney, Agent, or Firm* — Knobbe, Martens, Olson & Bear, LLP

(57) ABSTRACT

An alignment adapter for prosthetic sport feet, such as running feet, includes a male pyramid plate having a male pyramid, a female connector plate having a female connector, and a back plate. For use during alignment of a prosthetic running foot, the male pyramid plate is coupled to the back of a user's socket and the female connector plate and back plate are clamped about the foot. The male pyramid and female connector are coupled and adjusted relative to one another to achieve a desired alignment. The socket and foot are locked in an alignment fixture to maintain the alignment and the male pyramid, female connector, and back plates are removed. A laminated plate is coupled to the socket to maintain alignment during normal use.

15 Claims, 14 Drawing Sheets

(56) References Cited

U.S. PATENT DOCUMENTS

| | | | | |
|---|---|---|---|---|
| 5,047,063 A * | 9/1991 | Chen | A61F 2/64 | 403/59 |
| 5,116,382 A * | 5/1992 | Steinkamp | A61F 2/76 | 403/353 |
| 5,336,270 A | 8/1994 | Lloyd | | |
| 5,425,782 A * | 6/1995 | Phillips | A61F 2/76 | 403/87 |
| 5,443,526 A * | 8/1995 | Hoerner | A61F 2/76 | 411/531 |
| 5,458,657 A * | 10/1995 | Rasmusson | A61F 2/76 | 403/362 |
| 5,529,576 A | 6/1996 | Lundt et al. | | |
| 5,549,710 A * | 8/1996 | Vera | A61F 2/76 | 403/362 |
| 5,593,456 A | 1/1997 | Merlette | | |
| 5,653,767 A * | 8/1997 | Allen | A61F 2/66 | 623/52 |
| 5,653,768 A | 8/1997 | Kania | | |
| 5,728,176 A | 3/1998 | Phillips | | |
| 5,746,773 A * | 5/1998 | Littig | A61F 2/76 | 623/35 |
| 5,759,206 A * | 6/1998 | Bassett | A61F 2/76 | 403/113 |
| 5,800,565 A * | 9/1998 | Biedermann | A61F 2/76 | 623/27 |
| 5,888,217 A * | 3/1999 | Slemker | A61F 2/76 | 623/33 |
| 5,888,234 A * | 3/1999 | Littig | A61F 2/76 | 623/27 |
| 5,980,803 A * | 11/1999 | Slemker | A61F 2/5046 | 264/222 |
| 6,013,105 A * | 1/2000 | Potts | A61F 2/76 | 623/38 |
| 6,019,795 A | 2/2000 | Phillips | | |
| 6,033,440 A * | 3/2000 | Schall | A61F 2/76 | 403/84 |
| 6,051,026 A * | 4/2000 | Biedermann | A61F 2/76 | 623/27 |
| 6,228,124 B1 * | 5/2001 | Slemker | A61F 2/76 | 623/47 |
| 6,231,618 B1 | 5/2001 | Schall et al. | | |
| 6,458,163 B1 * | 10/2002 | Slemker | A61F 2/60 | 623/38 |
| 6,669,736 B2 * | 12/2003 | Slemker | B29C 41/20 | 264/222 |
| 6,692,533 B2 | 2/2004 | Johnson et al. | | |
| 6,872,347 B2 | 3/2005 | Johnson et al. | | |
| 6,893,468 B2 * | 5/2005 | Lund | A61F 2/78 | 623/33 |
| 7,083,654 B2 * | 8/2006 | Helenberger | A61F 2/76 | 623/33 |
| 7,108,722 B2 * | 9/2006 | Wagman | A61F 2/78 | 623/38 |
| 7,267,695 B2 * | 9/2007 | Curtis | A61F 2/76 | 623/38 |
| 7,318,504 B2 * | 1/2008 | Vitale | A61F 2/76 | 188/265 |
| 7,338,532 B2 | 3/2008 | Haberman et al. | | |
| 7,708,784 B2 | 5/2010 | Townsend et al. | | |
| D617,460 S * | 6/2010 | Okuda | D24/155 | |
| 7,946,782 B2 | 5/2011 | Curtis | | |
| 8,097,042 B2 * | 1/2012 | Slemker | A61F 2/5046 | 623/33 |
| 8,251,928 B2 * | 8/2012 | Pusch | A61F 2/76 | 600/595 |
| 8,845,755 B2 * | 9/2014 | Dillingham | A61F 2/60 | 403/87 |
| 8,910,534 B2 * | 12/2014 | Huang | B25B 5/006 | 33/655 |
| D723,692 S * | 3/2015 | Meyer | D24/155 | |
| D733,884 S * | 7/2015 | Hillmann | D24/155 | |
| D746,463 S * | 12/2015 | Meyer | D24/155 | |
| 9,474,633 B2 * | 10/2016 | Williams | A61F 2/64 | |
| 2002/0087216 A1 * | 7/2002 | Atkinson | A61F 2/66 | 623/38 |
| 2002/0143408 A1 | 10/2002 | Townsend | | |
| 2005/0049720 A1 | 3/2005 | Benson | | |
| 2005/0267600 A1 | 12/2005 | Haberman et al. | | |
| 2010/0061796 A1 | 3/2010 | Kurth | | |
| 2010/0161077 A1 | 6/2010 | Boone et al. | | |
| 2011/0015761 A1 | 1/2011 | Celebi et al. | | |
| 2011/0160871 A1 * | 6/2011 | Boone | A61F 2/60 | 623/26 |
| 2014/0005801 A1 * | 1/2014 | Van der Watt | A61F 2/76 | 623/53 |
| 2014/0031953 A1 * | 1/2014 | MacKenzie | A61F 2/68 | 623/34 |
| 2016/0058584 A1 * | 3/2016 | Cespedes | A61F 2/80 | 623/33 |

OTHER PUBLICATIONS

Imasen Engineering Corp. Lapoc Sports Samurai product, http://www.imasengiken.co.jp/en/lapoc/sport.html, believed to have been available by Jan. 23, 2012.

Otto Bock C-Sprint® product, Otto Bock Prosthetics—Lower Extremities Catalog, p. 102, 2008.

Extended Search Report in corresponding European Patent Application No. 13810443.5, dated Mar. 22, 2016, in 7 pages.

* cited by examiner

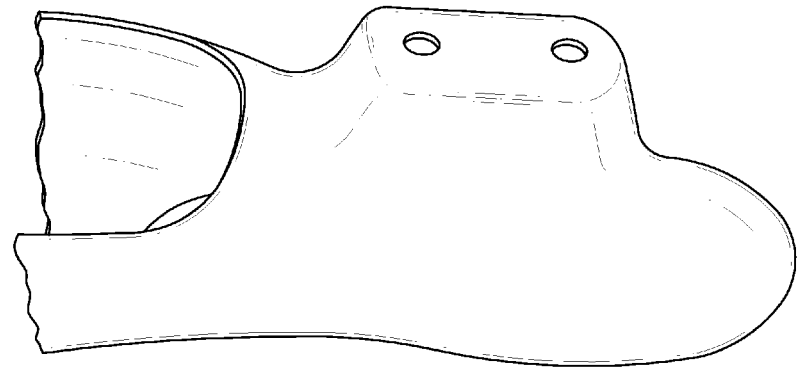
FIG.2
(PRIOR ART)
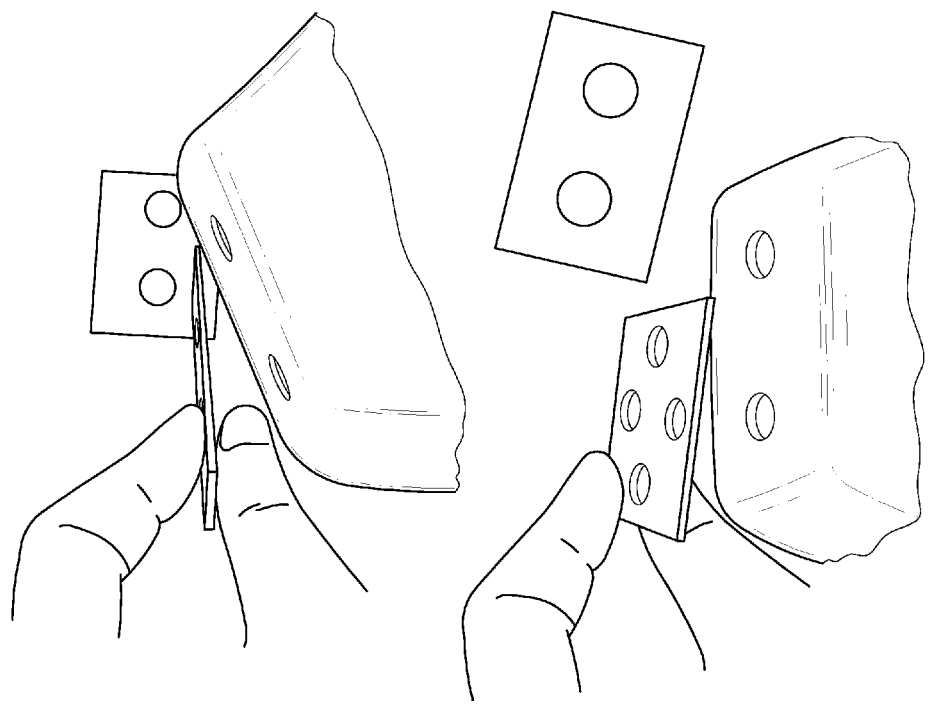

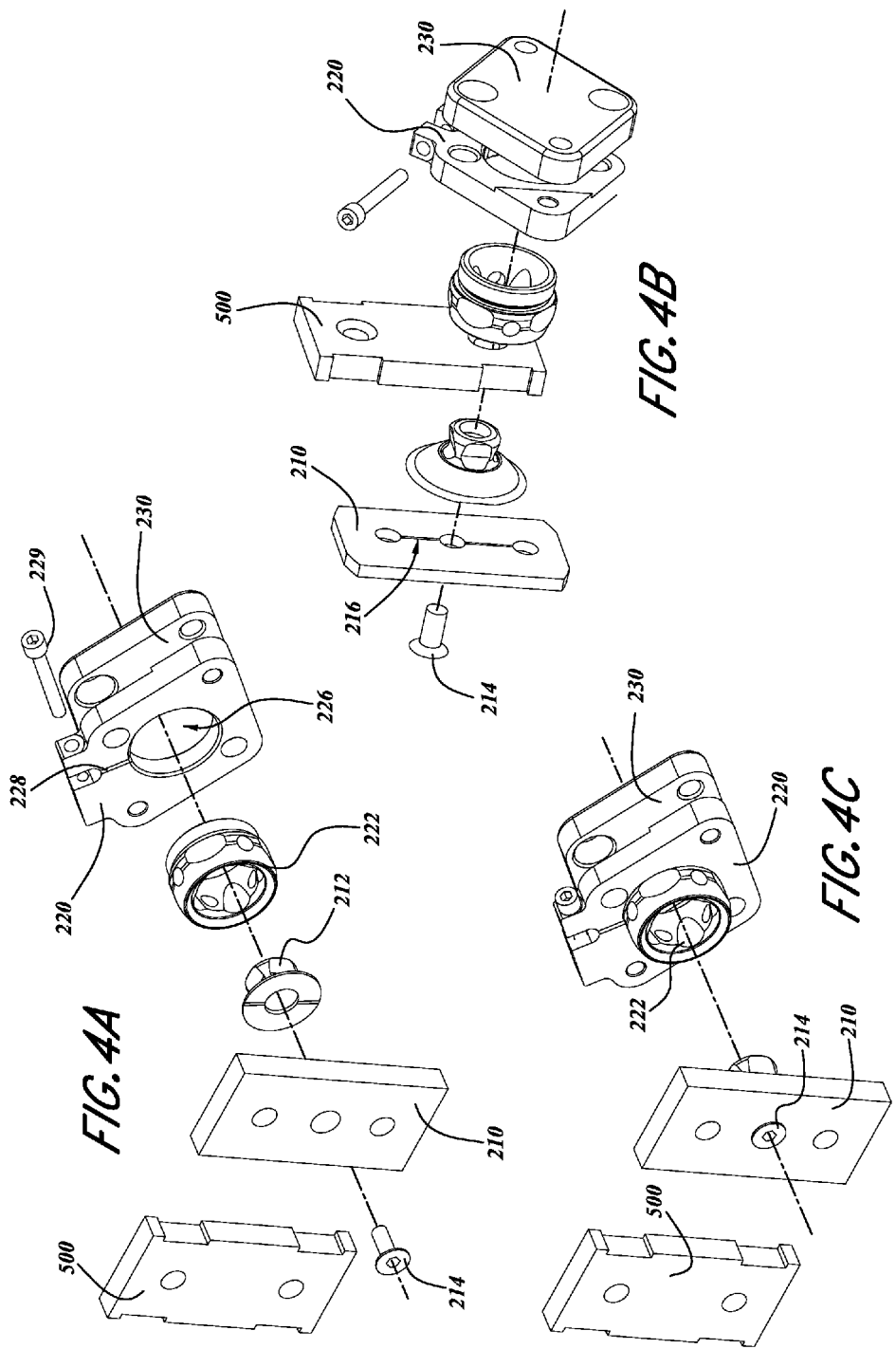

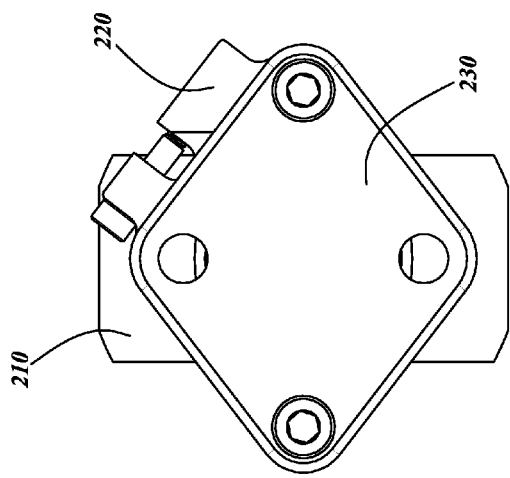
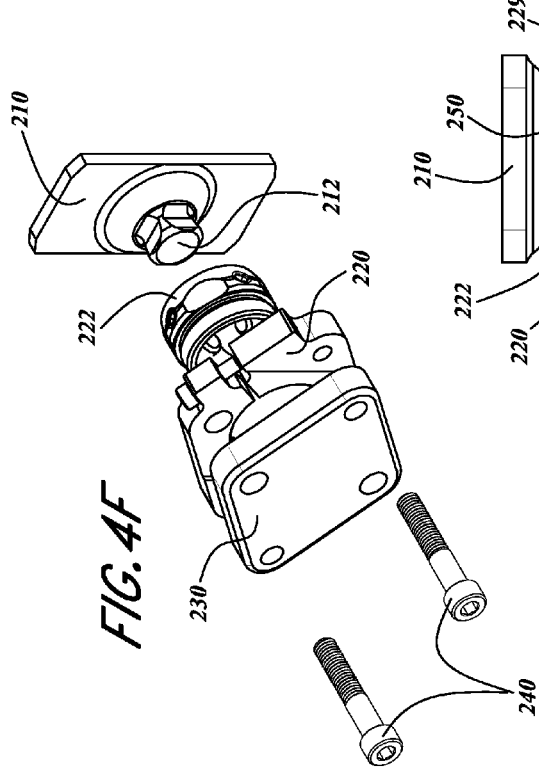
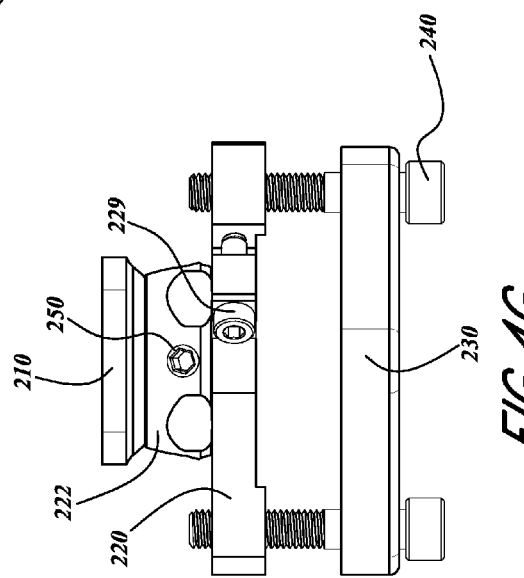

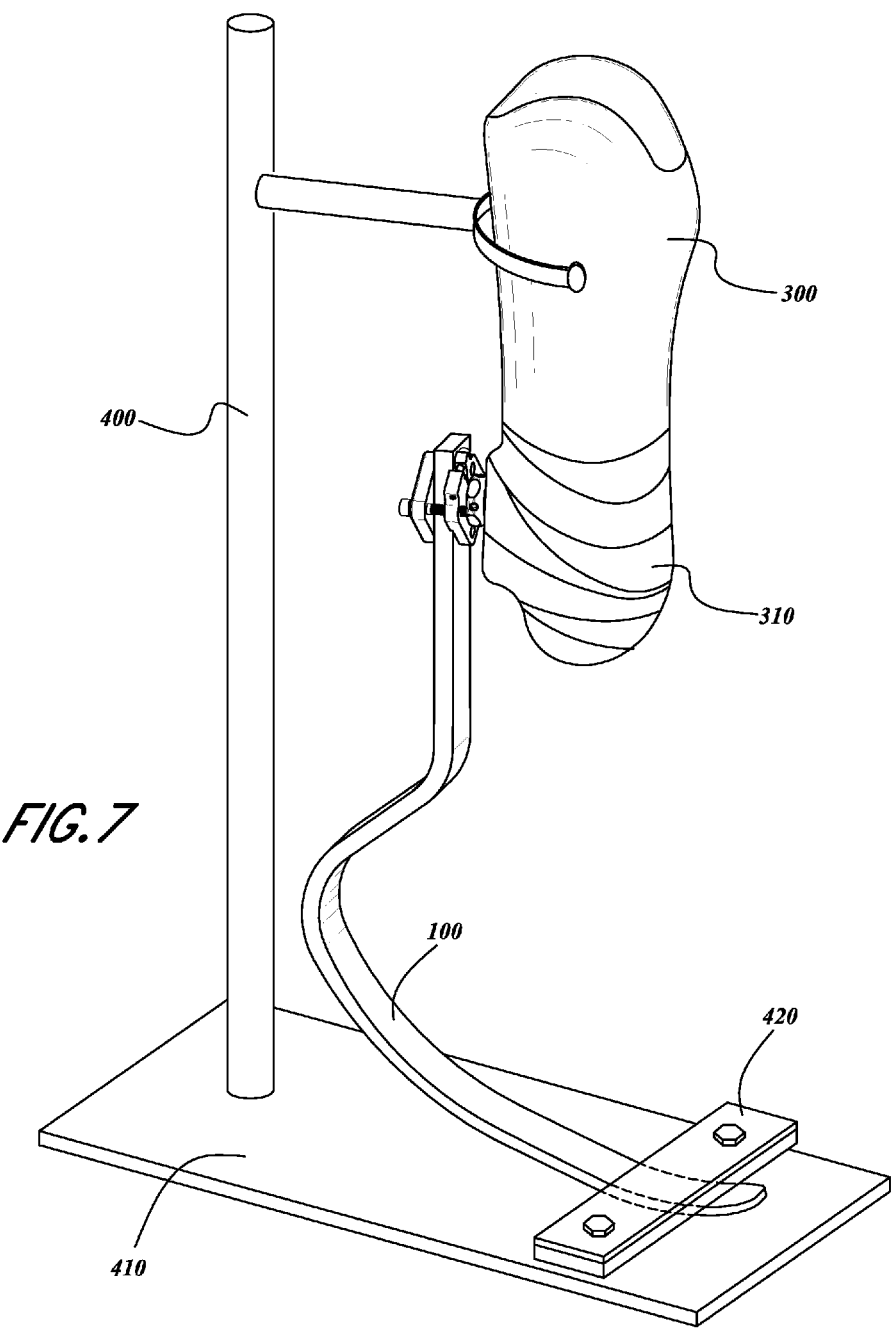

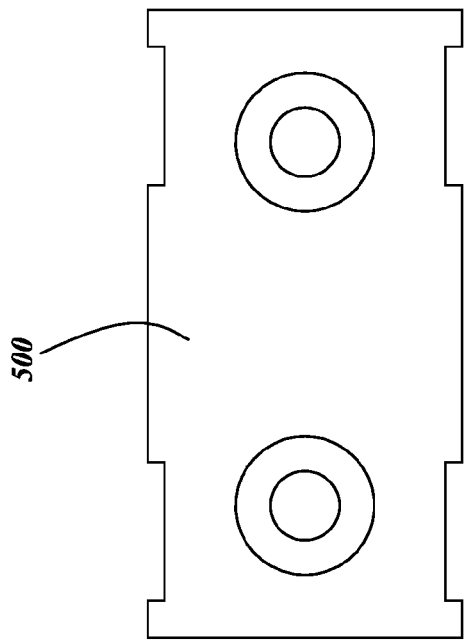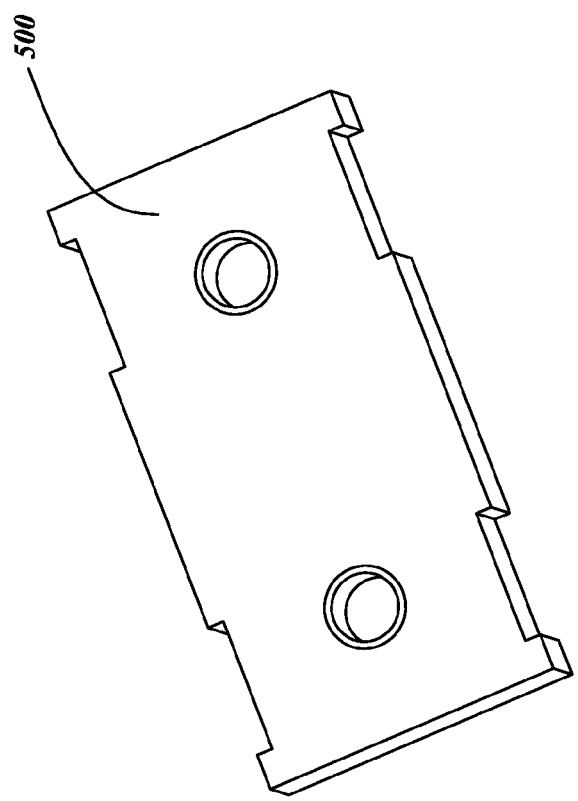
FIG. 8

ALIGNMENT ADAPTER FOR PROSTHETIC SPORT FEET

CROSS-REFERENCE TO RELATED APPLICATIONS

This application is a divisional application of U.S. application Ser. No. 13/928,210, filed Jun. 26, 2013, which claims priority benefit of U.S. Provisional Application No. 61/665,162, filed Jun. 27, 2012, the entirety of each of which is hereby incorporated by reference herein and should be considered a part of this specification.

BACKGROUND

Field

The present application relates to prosthetic adapters in general, and more particularly, to an alignment adapter for use with prosthetic sport feet.

Description of the Related Art

Various types of prosthetic foot devices are available as substitutes for human feet. Some prosthetic feet are designed especially for sporting activities such as running, both at the recreational and competitive levels. Prosthetic running feet are typically designed to efficiently store and release energy produced during running to improve performance. The alignment of prosthetic sport feet can affect the performance of the device and therefore the performance of the user athlete. For example, the alignment can affect the compression of the foot and the timing of the absorption and release of energy during use. Optimal alignment can reduce energy expenditure and reduce muscle and ligament fatigue and strain on the user.

Proper alignment includes determining the appropriate height, plantarflexion or dorsiflexion, inversion or eversion, and rotation of the foot relative to the socket. The prosthetist typically begins with initial bench alignment, and then makes further adjustments during dynamic alignment assessment. The prosthetist couples a lamination connector plate to the socket using plaster, a compound adhesive, or the like, then wraps the socket and plate with casting tape as shown in FIGS. 1A-1D. For some existing sport feet, the height is set by pre-drilling holes through the foot plate. If the height needs to be adjusted, new holes may need to be drilled through the foot. Additional holes can weaken the laminate, and in some cases the foot is scrapped. For other aspects of alignment, the prosthetist typically places wedges between the foot plate and lamination connector as shown in FIGS. 2 and 3. However, the use of alignment wedges can be time-consuming because the prosthetic components must be disassembled to make adjustments. Additionally, alignment wedges typically have pre-set angles, which can limit the range of angular adjustment possible during alignment.

SUMMARY

The alignment adapter described herein advantageously allows for improved alignment of prosthetic sport feet.

In some embodiments, a temporary alignment adapter for use with prosthetic feet includes a male pyramid plate, a female connector plate, and a back plate. The male pyramid plate includes a male pyramid and is configured to be temporarily coupled to a socket sized to receive a user's amputated leg. The female connector plate includes a female connector and is configured to be placed adjacent a front of a prosthetic foot proximate a proximal end of the prosthetic foot. The back plate is configured to be placed adjacent a back of the prosthetic foot proximate a proximal end of the prosthetic foot. The alignment adapter further includes one or more fasteners configured to couple the female connector plate and back plate. The fasteners are configured to extend alongside rather than through the prosthetic foot so that the female connector plate and back plate are clamped about the prosthetic foot. The male pyramid is configured to engage the female connector, and relative movement between the male pyramid and female connector adjusts alignment of the prosthetic foot relative to the socket.

In some embodiments, an alignment system for use with prosthetic feet includes a male pyramid plate, a female connector plate, and a back plate. The male pyramid plate includes a male pyramid and is configured to be temporarily coupled to a back of a socket sized to receive a user's amputated leg. The female connector plate includes a female connector and is configured to be placed adjacent a front of a prosthetic foot proximate a proximal end of the prosthetic foot. The female connector is removably coupleable to the male pyramid and in use, selectively fixed relative to the male pyramid to define a desired alignment between the prosthetic foot and the socket. The back plate is configured to be placed adjacent a back of the prosthetic foot proximate a proximal end of the prosthetic foot and removably coupled to the female connector plate about the prosthetic foot. The alignment system further includes a laminated plate configured to be coupled to the back of the socket to maintain the desired alignment during normal use and following removal of the male pyramid plate from the socket.

In some embodiments, a method of alignment a prosthetic foot includes attaching a male pyramid plate having a male pyramid to a back of a socket sized to receive a user's amputated leg. The method also includes placing a female connector plate having a female connector with set screws adjacent a front of a prosthetic foot proximate a proximal end of the prosthetic foot and placing a back plate adjacent a back of the prosthetic foot proximate the proximal end of the prosthetic foot. The method further includes coupling the female connector plate and back plate via fasteners extending alongside the prosthetic foot such that female connector plate and back plate are clamped about the prosthetic foot. In some embodiments, the method includes coupling the socket and the prosthetic foot to an alignment fixture, engaging the male pyramid and female connector, and adjusting the male pyramid and female connector relative to each other to obtain a desired alignment between the prosthetic foot and the socket. The method further includes setting the desired alignment by tightening the set screws of the female connector about the male pyramid and clamping the prosthetic foot to the alignment fixture to maintain the desired alignment.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIGS. 2-3 illustrate wedges used for prosthetic running foot alignment;

FIGS. 4A-4H illustrate components of an example alignment adapter;

FIG. 7 illustrates the assembly of FIG. 5 locked into an alignment jig; and

FIG. 8 illustrates laminate plates.

DETAILED DESCRIPTION

Figure 1A:
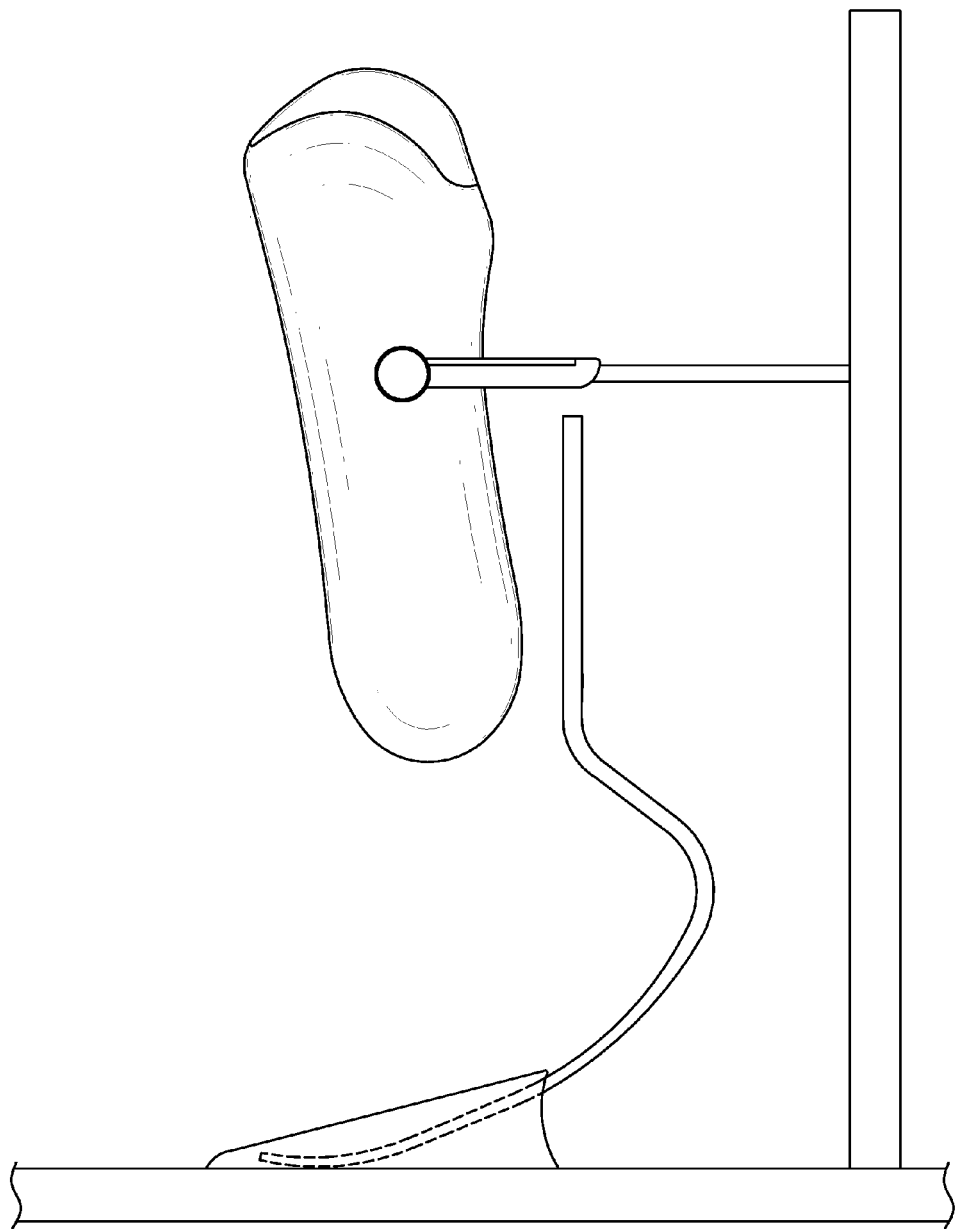
FIGS. 1A-1D illustrate a conventional method for aligning a prosthetic running foot relative to a socket.
Figure 1B:
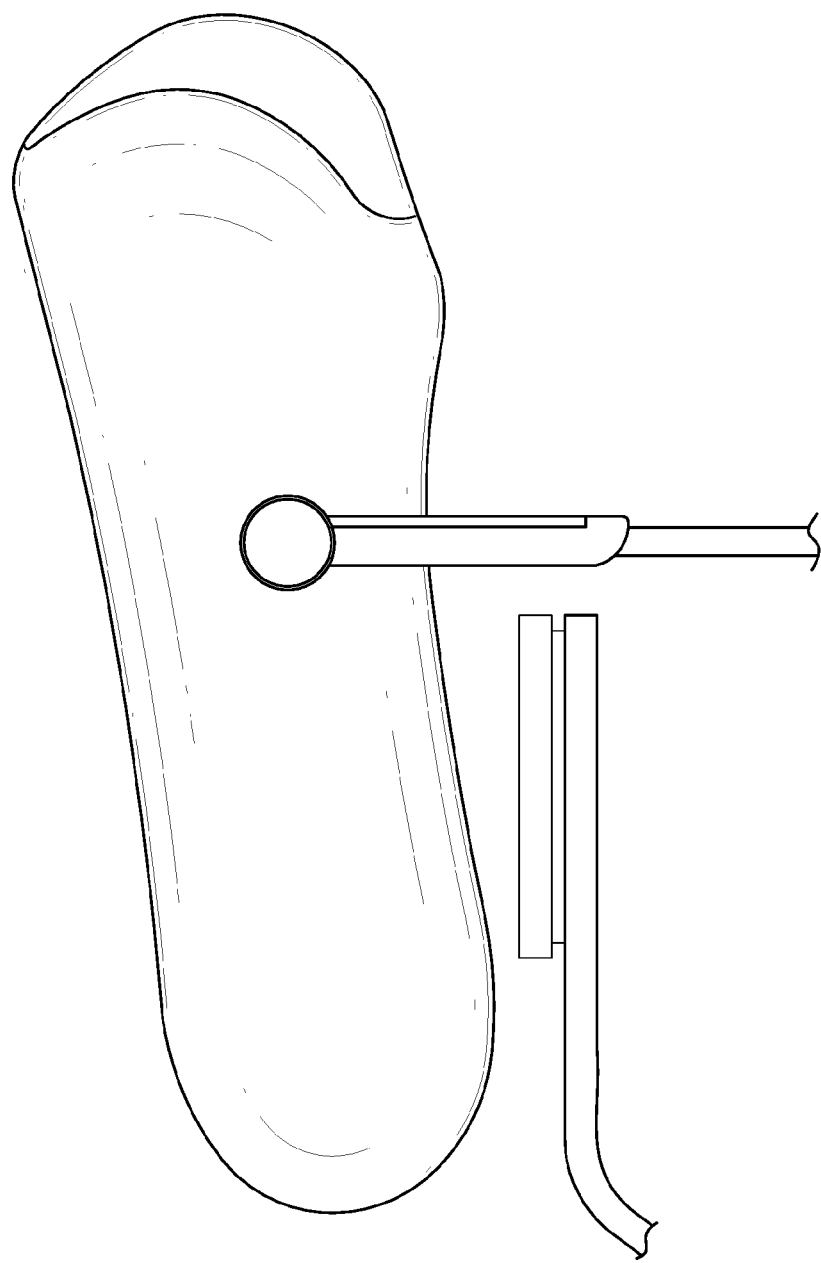
Figure 1C:
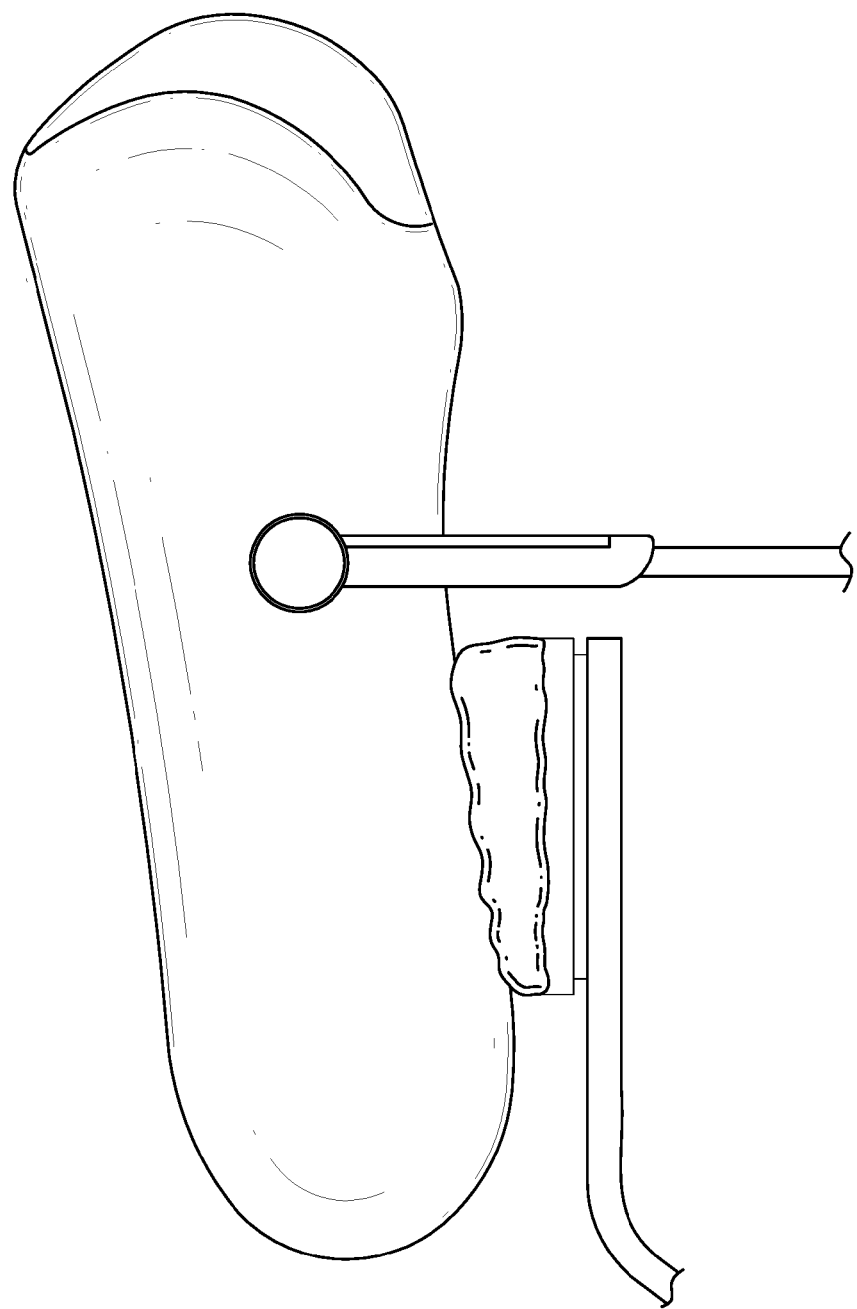
Figure 1D:
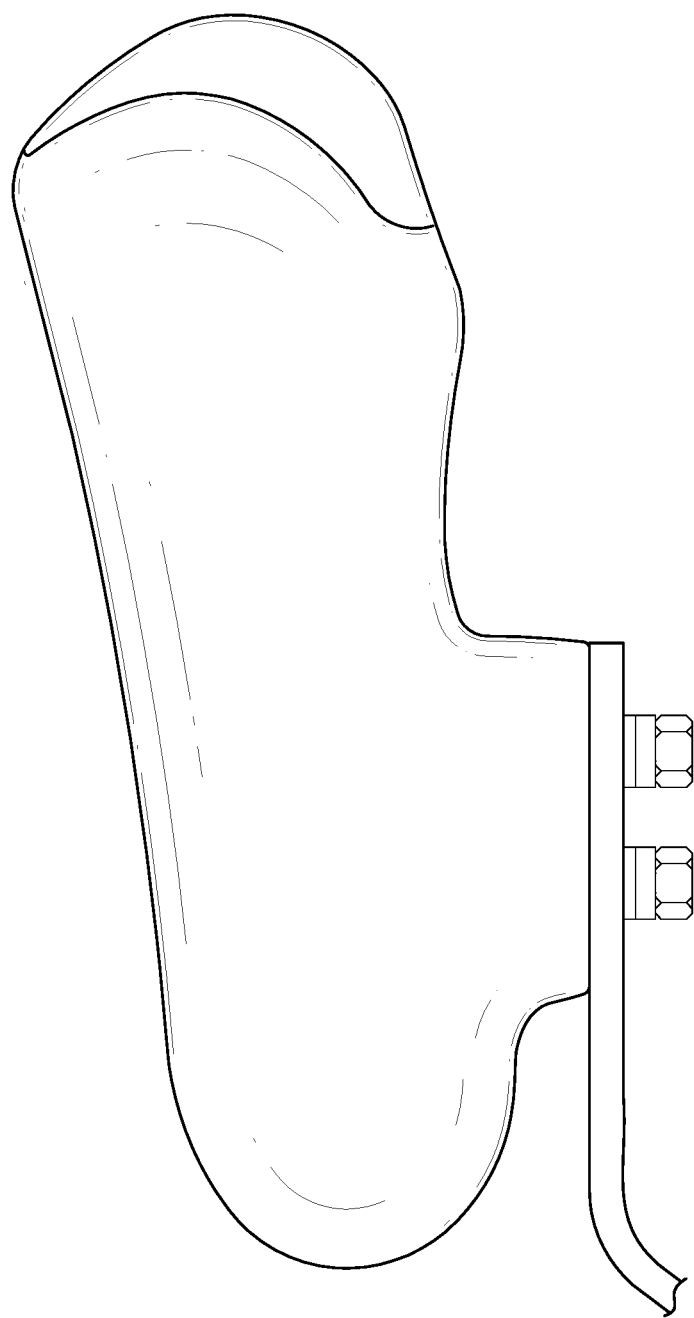
Figure 3:
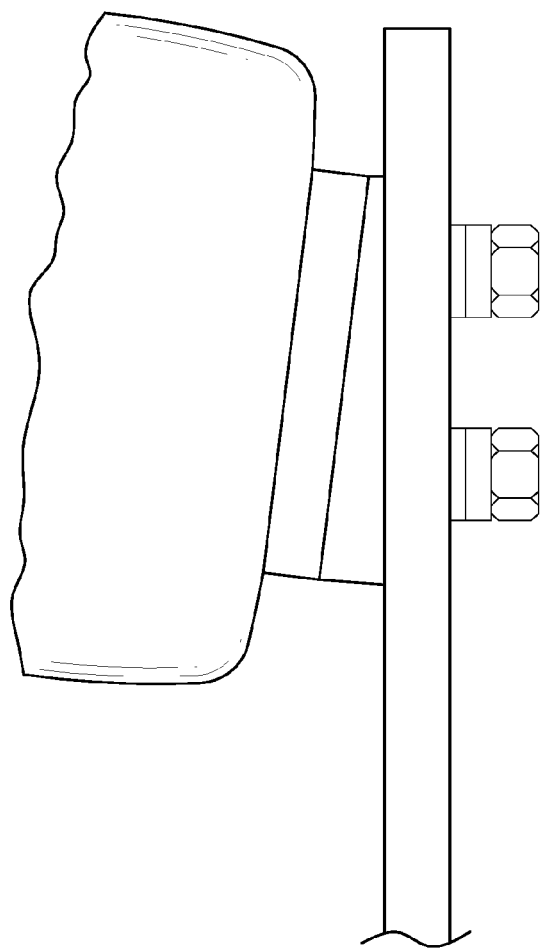
Figure 4E:
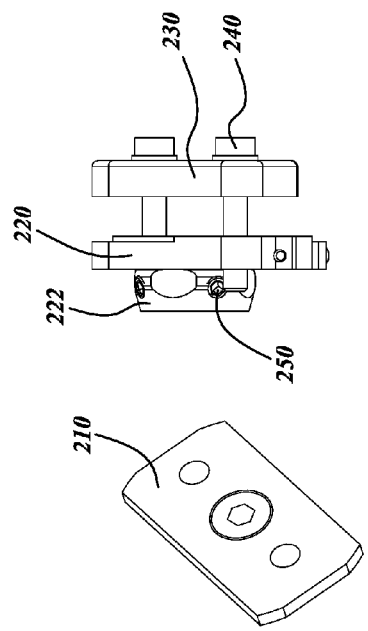
Figure 4D:
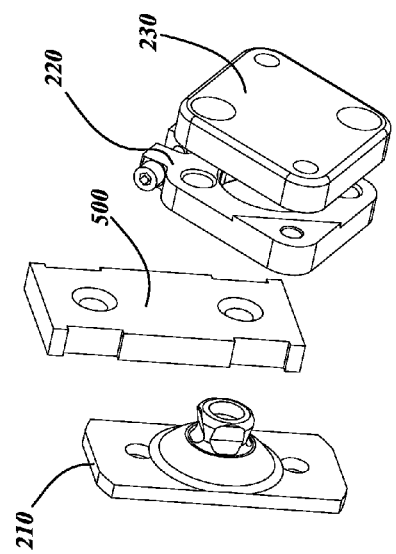

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

As shown in the example embodiment illustrated in FIGS. 4A-4H, an alignment adapter generally includes a male pyramid plate 210, a female connector plate 220, and a back plate 230. In the illustrated embodiment, the male pyramid plate 210 is generally rectangular and the female connector plate 220 and back plate 230 are generally square or diamond-shaped. However, other shapes are also possible. For example, the female connector plate 220 and back plate 230 can also be generally rectangular. In some embodiments, the male pyramid plate 210 is made of aluminum. However, other suitable materials can be used. In some embodiments, the male pyramid plate 210 has a thickness of about 10.00 mm, though it can have other suitable dimensions greater or smaller than this. The male pyramid plate 210 includes a male pyramid 212, and the female connector plate 220 includes a female connector 222 configured to receive the male pyramid 212.

As shown in FIGS. 4A-4C, the male pyramid 212 can be coupled to the male pyramid plate 210 via a screw or bolt 214 extending through the male pyramid plate 210 and into the male pyramid 212. In some embodiments, the male pyramid plate 210 includes a stripe, groove, or protrusion 216 configured to inhibit rotation of the male pyramid 212 relative to the male pyramid plate 210 by engaging a corresponding stripe, groove, or protrusion on a back surface of the male pyramid 212. As shown in FIGS. 4A-4C, the female connector plate 220 can include a bore 226 configured to receive the female connector 222. The female connector plate 220 can further include a slit 228 extending from the bore 226 to an outer edge of the female connector plate 220. The female connector 222 can be coupled to the female connector plate 220 by inserting the female connector 222 into the bore 226 and inserting a screw 229 into the female connector plate 220 across the slit 228 to tighten the female connector plate 220 around the female connector 220. The female connector 222 includes set screws 250 configured to fix a position and/or orientation of the male pyramid 212 relative to the female connector 222 when the male pyramid 212 is inserted in the female connector 222. In the illustrated embodiment, the female connector 222 includes four set screws 250.

In some embodiments, the female connector plate 220 includes at least two holes 224 located generally across the female connector 222 from one another. In the illustrated embodiment, the female connector plate 220 includes four holes 224 located at the corners of the female connector plate 220 and substantially equally spaced around the female connector 222 from one another. Other numbers, spacing, and configurations of holes 224 are also possible. The back plate 230 can also include at least two holes 232 configured to align with the holes 224 of the female connector plate 220. In the illustrated embodiment, the back plate 230 also includes four holes 232 located at the corners of the back plate 230.

Figure 5:
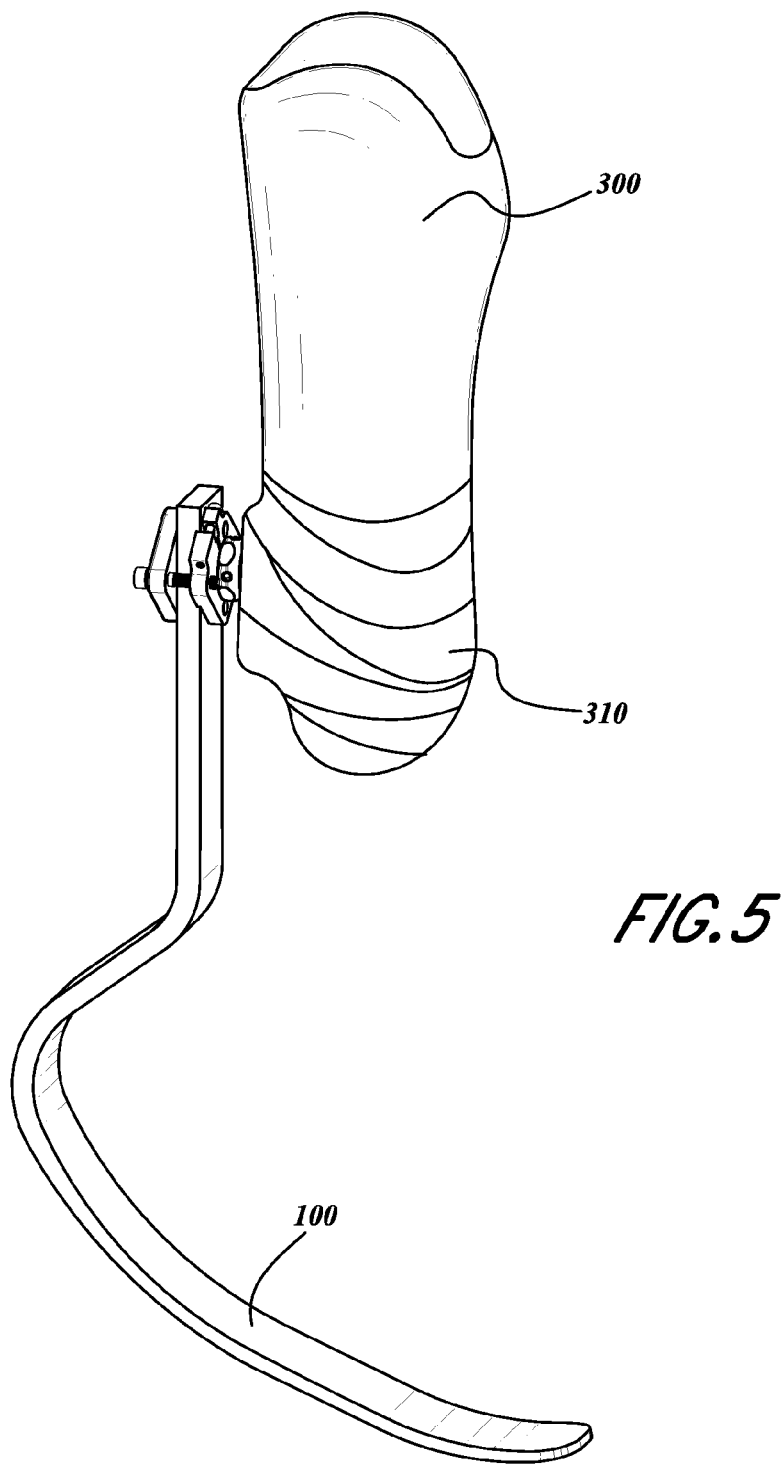
FIG. 5 illustrates the alignment adapter components of FIGS. 4A-4H coupled to a prosthetic socket and prosthetic running foot.
Figure 6A:
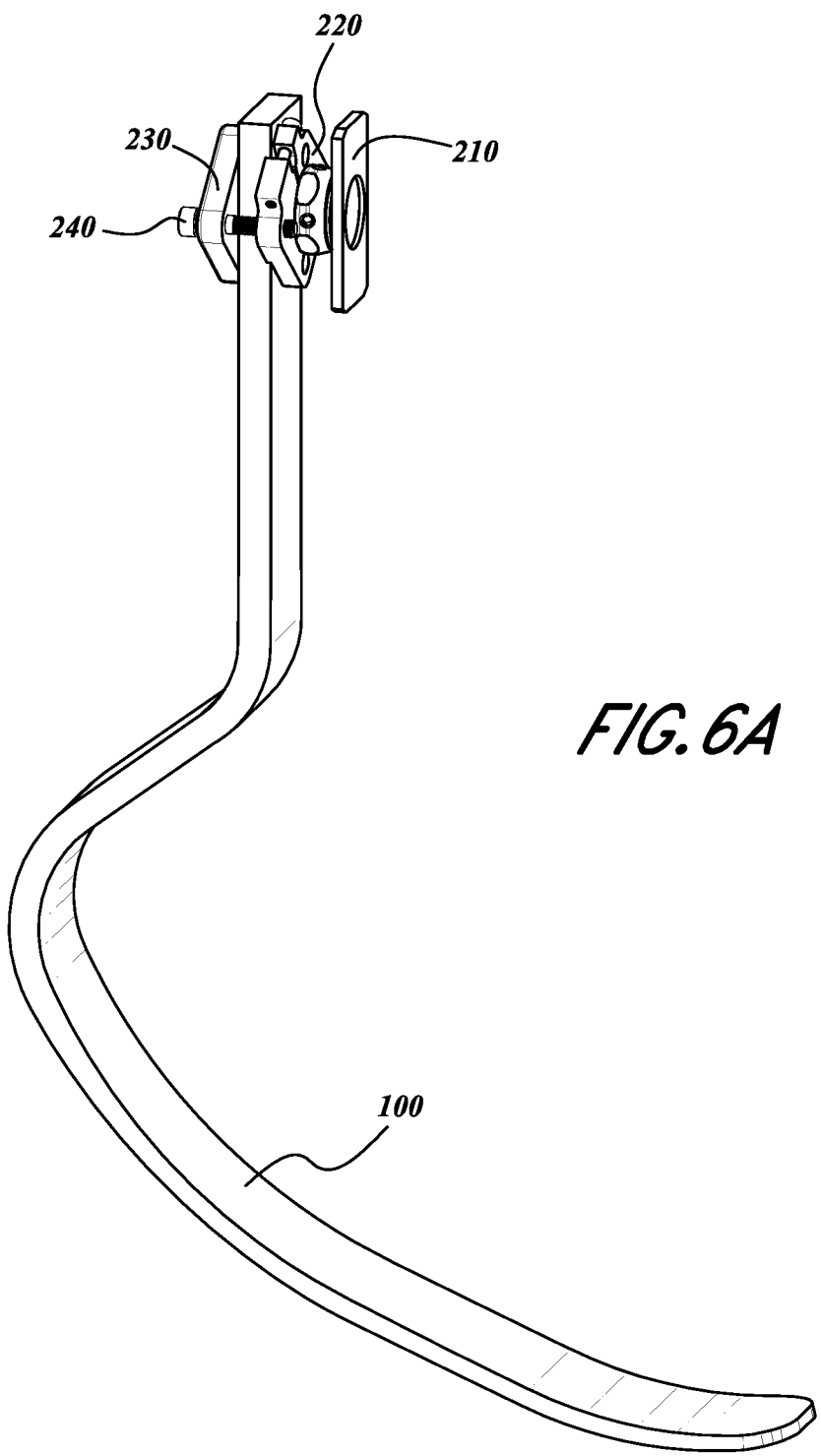
FIGS. 6A-6C illustrate the alignment adapter components of FIGS. 4A-4H coupled to a prosthetic running foot.
Figure 6C:
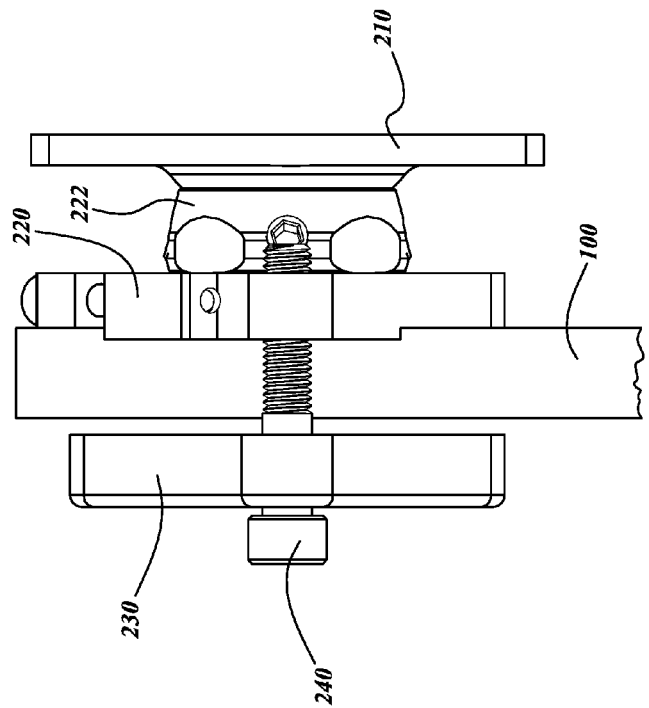
Figure 6B:
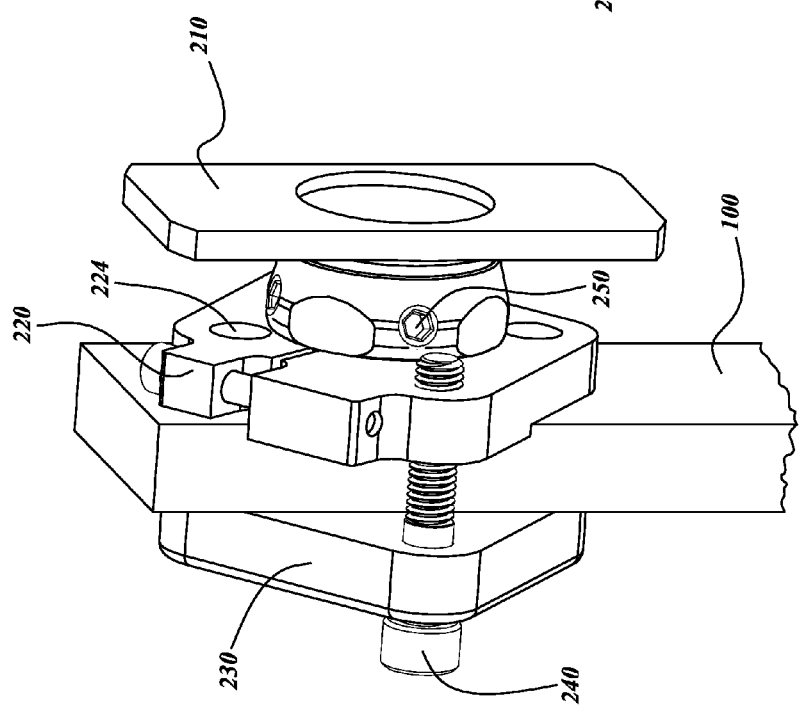

In some embodiments, to use the alignment adapter during bench alignment of a prosthetic foot, such as a prosthetic running foot 100, the male pyramid plate 210 is coupled to the back of the user's socket 300 so that the male pyramid 212 extends rearwardly from the socket 300. For example, the male pyramid plate 210 can be lightly bonded to the back of the socket 300 using plaster, a compound adhesive, or the like and wrapped with casting tape 310 as shown in FIG. 5. The female connector plate 220 and back plate 230 are placed adjacent to the front and back sides of the foot 100, respectively, so that the female connector 222 extends forward from the foot 100. The female connector plate 220 and back plate 230 are coupled via fasteners 240 (e.g., screws, bolts, clamps, etc.) placed through two pairs of the aligned holes 224, 232 of the female connector 220 and back 230 plates, respectively, as shown in FIGS. 5-6C. The female connector plate 220, back plate 230, and holes 224, 232 are configured and aligned so that the fasteners 240 extend beside rather than through the foot 100. Thus, no holes need to be drilled through the foot 100 during alignment (e.g., the adapter is clamped about the foot). Advantageously, the alignment, for example, the height, of the female connector plate 220 and back plate 230 on the foot 100 can be changed without having to drill holes through the foot every time the alignment is changed, thereby reducing material waste and the need to scrap the prosthetic foot 100 during the alignment process.

Alternatively, in some embodiments, the female connector plate 220 and back plate 230 can be coupled about the foot 100 via clamps, vises, or other clamping mechanisms. In such embodiments, holes 224, 232 in the female connector 220 and back 230 plates, respectively, for fasteners 240 may not be required. In some embodiments, the female connector plate 220 can be clamped directly to the front of the foot 100 without a back plate 230. In some embodiments, the orientation and arrangement of the adapter components can be reversed, for example, so that a female connector 220 is coupled to the back of the socket 300 and a male pyramid 212 is coupled to the front of the foot 100.

To align the sport foot using the alignment adapter, the socket 300 with the male pyramid plate 210 and foot 100 with female connector 220 and back 230 plates are coupled to an alignment fixture 400 as shown in FIG. 7. The male pyramid 212 and female connector 222 are coupled and adjusted relative to each other (e.g., angular orientation) to achieve a desired alignment. The set screws 250 on the female connector 222 are used to grip the male pyramid 212 in that particular orientation. The foot 100 is then clamped to a bottom plate 410 of the alignment fixture 400 via a clamp 420 to fix the position and alignment of the foot 100 relative to the socket 300.

The alignment adapter described herein is temporary and only coupled to the foot during alignment. When the appropriate alignment has been determined, a laminated plate 500 replaces the alignment adapter to maintain alignment between the socket and prosthetic foot during normal use. This advantageously helps reduce the overall weight of the user's leg and foot.

Once the desired height and alignment are determined and the components are locked in the alignment fixture 400, the prosthetist can drill attachment holes in the foot 100 through the remaining open holes 232 in the back plate 230. The holes 232 can be spaced and positioned to advantageously allow for easy drilling of attachment holes in the foot at appropriate locations and spacing. The prosthetist can then remove the alignment adapter components from the foot 100 and socket 300 while the alignment fixture 400 maintains the desired alignment. The prosthetist then aligns the laminated plate or lamination connector 500, shown in FIG. 8, with the foot 100 and attaches the plate 500 to the socket 300 using plaster, a compound adhesive, or the like to build up the socket as needed. Fasteners, e.g., bolts, are used to couple the foot 100 to the laminated plate 500 for normal use.

As discussed herein, the alignment adapter is used during alignment of a prosthetic sport foot and then removed and replaced with a laminated plate for normal use. The use of the male pyramid 212 and female connector 222 allows for easier and more precise alignment, and the removal of these components after alignment helps reduce the weight and bulk of the foot assembly during use.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. An alignment system for use with prosthetic feet, the system comprising:
    a male pyramid plate having a male pyramid and configured to be temporarily coupled to a back of a socket sized to receive a user's amputated leg;
    a female connector plate having a bore and a female connector at least partially disposed in the bore, the female connector plate configured to be placed adjacent a front of a prosthetic foot proximate a proximal end of the prosthetic foot, the female connector removably coupleable to the male pyramid and selectively fixed relative to the male pyramid to define a desired alignment between the prosthetic foot and the socket, the female connector plate further including at least one fastening opening positioned laterally outward from the bore;
    a back plate including at least one fastening opening corresponding to the at least one fastening opening on the female connector plate, the back plate configured to be placed adjacent a back of the prosthetic foot proximate a proximal end of the prosthetic foot and removably coupled to the female connector plate about the prosthetic foot via at least one fastener extending through the at least one fastening openings on the female connector plate and back plate; and
    a laminated plate configured to be coupled to the back of the socket to maintain the desired alignment during normal use and following removal of the male pyramid plate from the socket.

2. The alignment system of claim 1, wherein the at least one fastener is configured to extend alongside rather than through the prosthetic foot so that the female connector plate and back plate are clamped about the prosthetic foot.

3. The alignment system of claim 2, wherein the fastener comprises a screw.

4. The alignment system of claim 2, wherein the fastener comprises a bolt.

5. The alignment system of claim 2, wherein the at least one fastener comprises two fasteners and the female connector plate comprises at least two fastening openings disposed on either side of the female connector, each configured to receive one of the fasteners.

6. The alignment system of claim 5, wherein the back plate comprises at least two fastening openings corresponding to the at least two fastening openings of the female connector plate such that a spacing between the at least two fastening openings of the back plate is approximately equal to a spacing between the at least two fastening openings of the female connector plate, the at least two fastening openings configured to receive the fasteners.

7. The alignment system of claim 5, wherein the female connector plate comprises two holes configured to be open to allow for the drilling of holes in the prosthetic foot, the two holes spaced apart from the female connector and positioned along an axis perpendicular to an axis defined by the two fastening openings.

8. The alignment system of claim 7, wherein the female connector plate is diamond-shaped and each of the two fastening openings and two holes is located proximate a corner of the female connector plate.

9. The alignment system of claim 6, wherein the back plate comprises two holes configured to be open to allow for the drilling of holes in the prosthetic foot, the two holes positioned along an axis perpendicular to an axis defined by the two fastening openings.

10. The alignment system of claim 9, wherein the back plate is diamond-shaped and each of the two fastening openings and two holes is located proximate a corner of the back plate.

11. The alignment system of claim 1, wherein the female connector comprises set screws configured to be tightened about the male pyramid to maintain a desired alignment of the prosthetic foot relative to the socket.

12. The alignment system of claim 1, wherein the female connector plate comprises two holes configured to be open to allow for the drilling of holes in the prosthetic foot.

13. The alignment system of claim 12, wherein the laminated plate comprises two holes and a spacing between the two holes of the female connector plate is approximately equal to a spacing between the two holes of the laminated plate.

14. The alignment system of claim 1, wherein the back plate comprises two holes configured to be open to allow for the drilling of holes in the prosthetic foot.

15. The alignment system of claim 14, wherein the laminated plate comprises two holes and a spacing between the two holes of the back plate is approximately equal to a spacing between the two holes of the laminated plate.

* * * * *